United States Patent [19]

Duffett et al.

[11] Patent Number: Plant 5,324

[45] Date of Patent: Nov. 6, 1984

[54] CHRYSANTHEMUM PLANT NAMED DEBONAIR

[75] Inventors: William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 435,694

[22] Filed: Oct. 21, 1982

[51] Int. Cl.[3] ..... A01H 5/00

[52] U.S. Cl. ..... Plt./76

[58] Field of Search ..... Plt./76

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Debonair having flat capitulum form, decorative capitulum type, purple ray floret color, diameter across face of capitulum up to 55 mm., short plant height, compact, spreading branching pattern, average natural season flowering date of Sept. 15, and average flowering response period of seven (7) weeks in photoperiodic controlled short day programs.

3 Drawing Figures

The present invention comprises a new and distinct cultivar of *Chrysanthemum morifolium*, Ramat., hereinafter referred to by the cultivar named Debonair.

Debonair is a product of a planned breeding program which had the objective of creating cultivars with decorative capitulum type, medium height, spreading branching pattern, durable inflorescence, seven (7) week flowering response period, and purple ray floret color under outdoor natural season conditions.

Debonair was originated from a cross made by Grace H. Mack in a controlled breeding program in New Canaan, Conn. in the year 1978. The female parent was 4080, a salmon pink decorative, an unnamed seedling selected from a cross of M4570×M859. The male parent was M712, an orange bronze decorative, an unnamed seedling selected from a cross of M539×3363.

Debonair was discovered and selected as a flowering plant within the progeny of the stated cross by William E. Duffett in 1979 in an outdoor field in Salinas, Calif. The first act of asexual reproduction of Debonair was accomplished when vegetative cuttings were taken from the initial selection in Salinas, Calif. by William E. Duffett. Horticultural examination of selected units initiated July 1980 has demonstrated that the combination of characteristics herein disclosed for Debonair are firmly fixed and are retained through successive generations of asexual reproduction.

Debonair has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Debonair which in combination distinguish this chrysanthemum as a new and distinct cultivar:

(1) Flat capitulum form.
(2) Decorative capitulum type.
(3) Purple ray floret color.
(4) Diameter across face of capitulum up to 55 mm.

(5) Short plant height.
(6) Compact, spreading branching pattern.
(7) Average natural season flowering date of Sept. 15.
(8) Average flowering response period of seven (7) weeks in photoperiodic controlled flowering programs.

The accompanying photographic drawings show typical inflorescence and foliage characteristics of Debonair. Sheet 1 is a color photograph of Debonair. Sheet 2 is a black and white photograph showing three views of the inflorescence of Debonair. Sheet 3 is a black and white photograph showing the leaves of Debonair at three stages of growth (mature, intermediate, immature).

Of the many commercially available cultivars known to the present inventors, the most similar existing cultivar in comparison to Debonair is the purple cultivar Tinkerbell, an unpatented cultivar.

Reference is made to attached Chart A which compares certain characteristics of Debonair with the same characteristics of Tinkerbell. It will be noted that in comparison to Tinkerbell, Debonair has superior inflorescence and color durability, later natural season flower date, and larger diameter across face of capitulum. The capitulum form, capitulum type, plant height, ray floret color, branching pattern, and plant spread of Debonair are similar to those characteristics of Tinkerbell.

In the following description, color references are made to The Royal Horticultural Society Colour Chart. The color values were determined between 2:45 and 3:00 P.M. on Sept. 15, 1981 under 150 foot-candle light intensity at Salinas, Calif.

Botanical classification: *Chrysanthemum morifolium*, Ramat., cv Debonair.

INFLORESCENCE

Capitulum:

*Form.*—Flat.

*Type.*—Decorative.

*Permanence.*—3 To 4 weeks.

*Diameter across face.*—45 To 55 mm.

Corolla of ray florets:

*Color (abaxial).*—78C Immature to 78D mature.

*Color (adaxial).*—186D.

Reproductive organs:

*Androecium.*—Present disc florets; pollen scant.

*Gynoecium.*—Present both ray and disc florets.

*Corolla of disc florets:*

*Color.*—14A.

PLANT

General appearance: Compact with spreading branching pattern.

Foliage:

*Color (abaxial).*—147A.

*Color (adaxial).*—147B.

CHART A

Comparison Of Debonair and Tinkerbell

| Cultivar | Ray Floret Color | Capitulum Form and Type | Average Natural Season Flower Date |
|---|---|---|---|
| Debonair | Purple | Flat Decorative | September 15 |
| Tinkerbell | Purple | Flat Decorative | September 5 |

| Cultivar | Plant Height | Branching Pattern and Spread | Diameter Across Face Of Capitulum | Permanence Of Form and Color |
|---|---|---|---|---|

CHART A-continued

Comparison Of Debonair and Tinkerbell

| | | | | |
|---|---|---|---|---|
| Debonair | Short | Compact Spreading | 45 to 55 mm. | 3 to 4 Weeks Firm Inflorescence Color Resists Fading |
| Tinkerbell | Short | Compact Spreading | 30 to 45 mm. | 1 to 2 Weeks Soft Inflorescence Color Rapidly Fades |

Comparisons Made Of Plants Grown Under Natural Season Outdoor Field Conditions in Salinas, California

We claim:

1. A new and distinct cultivar of *Chrysanthemum morifolium,* Ramat., plant known by the name Debonair, as described and illustrated, and particularly characterized as to uniqueness by the combined characteristics of flat capitulum form, decorative capitulum type, durable inflorescence, purple ray floret color, diameter across face of capitulum up to 55 mm., short plant height, compact, spreading branching pattern, average natural season flowering date of Sept. 15, and average flowering response period of seven (7) weeks in photoperiodic controlled short day programs.

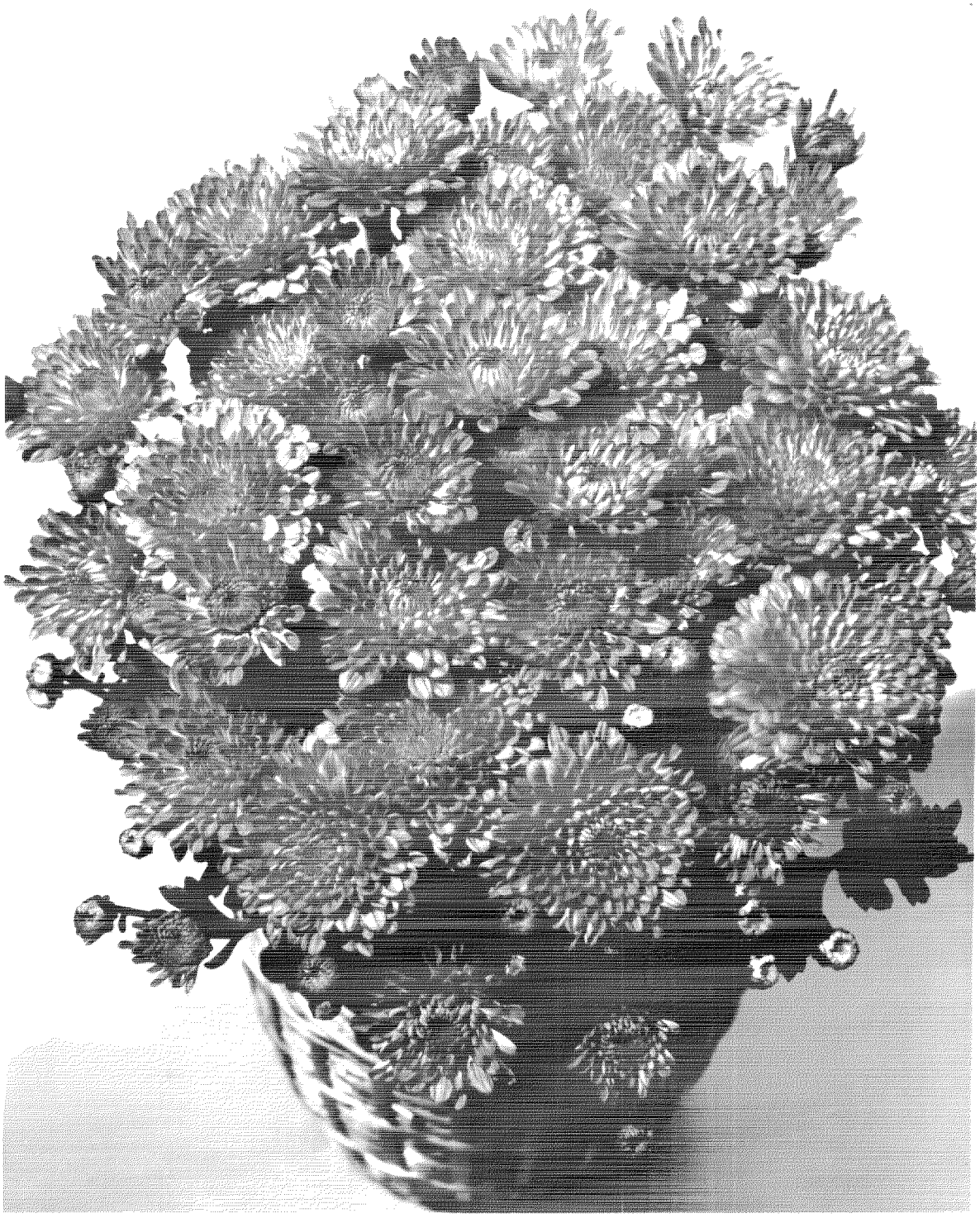

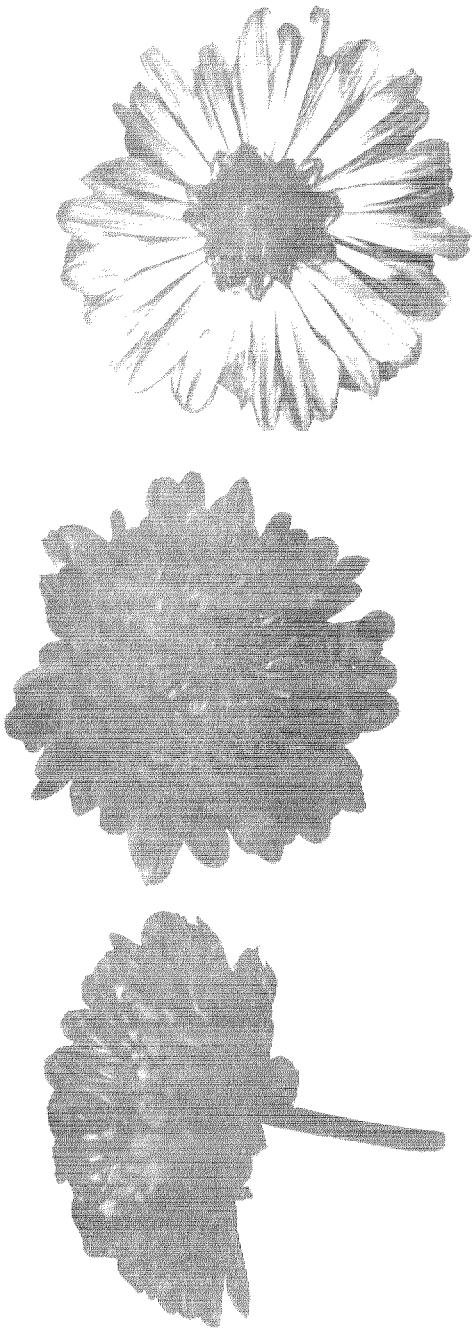

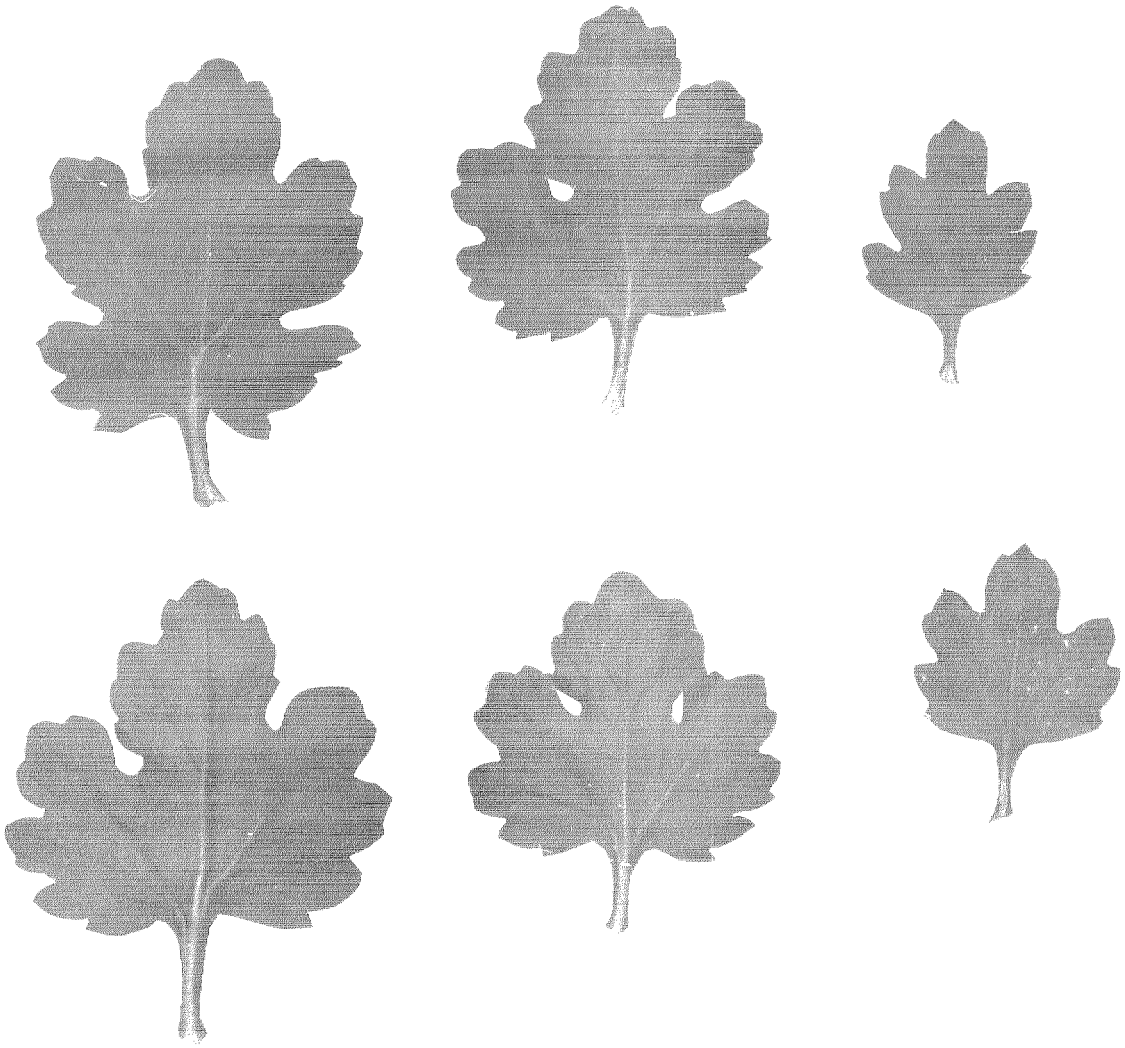

* * * * *